United States Patent [19]
Farkas

[11] Patent Number: 5,217,436
[45] Date of Patent: Jun. 8, 1993

[54] REMOTE CANNULA REMOVAL CARTRIDGE SYRINGE

[76] Inventor: Paul J. Farkas, 2 Mill St., Princeton, Me. 04668

[21] Appl. No.: 833,455

[22] Filed: Jan. 21, 1992

[51] Int. Cl.⁵ .................... A61M 5/00; A61M 5/50
[52] U.S. Cl. .................... 604/187; 604/234; 604/110
[58] Field of Search ........... 604/110, 187, 188, 197, 604/198, 199, 232, 240, 242, 243, 263

[56] References Cited

U.S. PATENT DOCUMENTS

| | | | |
|---|---|---|---|
| 1,607,271 | 11/1926 | Smith | 604/234 |
| 1,718,592 | 6/1929 | Smith | 604/234 |
| 2,956,563 | 10/1960 | Sarnoff | 604/232 |
| 3,648,695 | 3/1972 | Bowen | |
| 4,568,336 | 2/1986 | Cooper | 604/240 |
| 4,840,619 | 6/1989 | Hughes | 604/187 |
| 4,904,244 | 2/1990 | Harsh et al. | 604/187 |
| 4,915,701 | 4/1990 | Halkyard | 604/198 |
| 4,931,040 | 6/1990 | Haber et al. | 604/110 |
| 4,932,940 | 6/1990 | Walker et al. | 604/110 |
| 4,950,253 | 8/1990 | Jacobs | 604/218 |
| 4,986,811 | 1/1991 | Thead et al. | 604/110 |
| 4,986,812 | 1/1991 | Perler | 604/110 |
| 5,112,307 | 5/1992 | Haber et al. | 604/110 |
| 5,116,319 | 5/1992 | van den Haak | 604/110 |
| 5,154,698 | 10/1992 | Compagnucci et al. | 604/110 |

Primary Examiner—John D. Yasko
Assistant Examiner—Adam J. Cermak
Attorney, Agent, or Firm—Robert M. Sperry

[57] ABSTRACT

A remote cannula removal cartridge syringe comprising a first barrel, a second barrel, an expandable needle hub, and a modified needle hub receiver. The second barrel is concentric with the first barrel and has a retaining pin which slides within a series of grooves of the first barrel. After use of the syringe the second barrel may be protracted causing the engagement and safe separation of the needle hub from the syringe without requiring the operator to recap the syringe or place fingers near the contaminated needle.

15 Claims, 2 Drawing Sheets

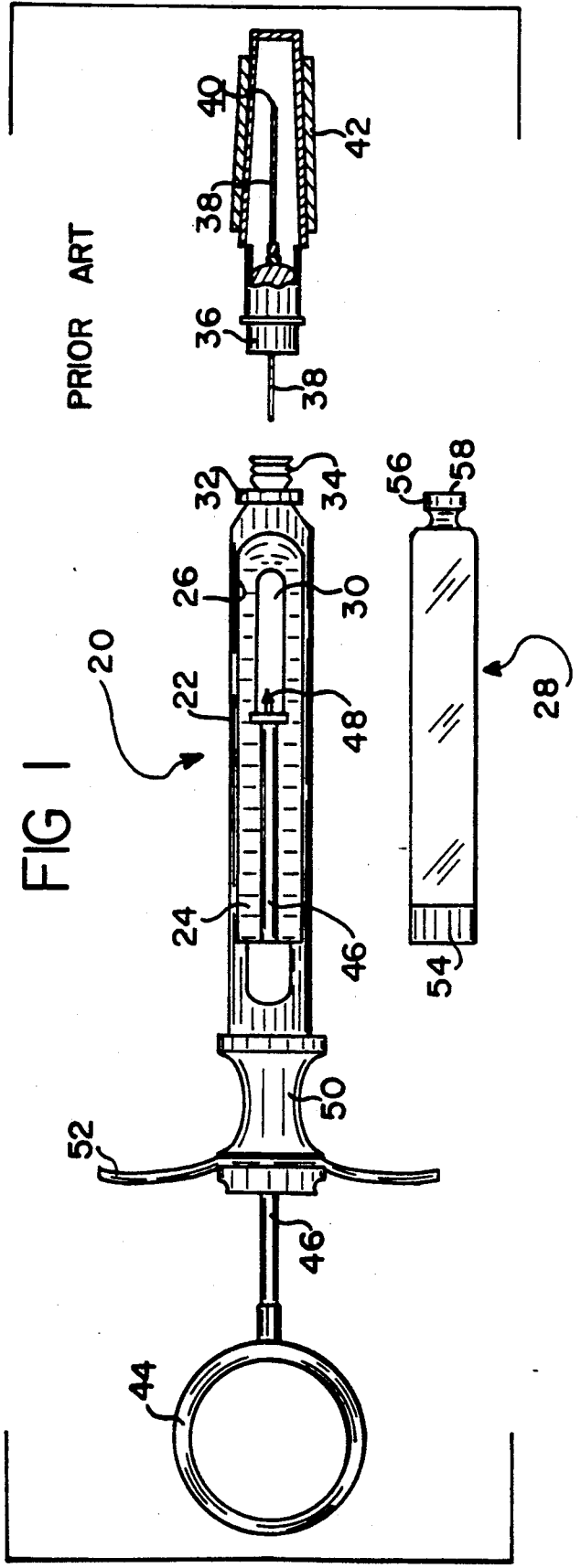

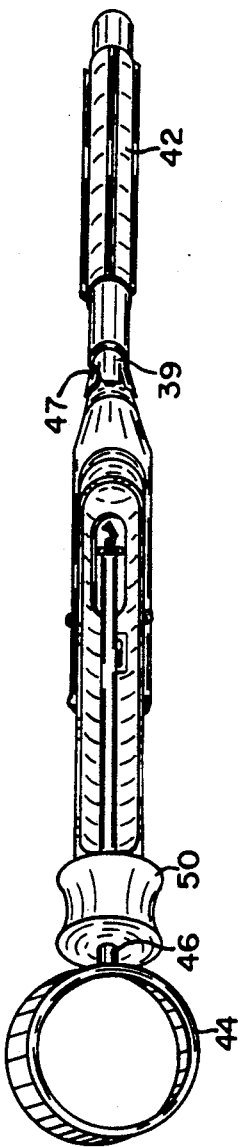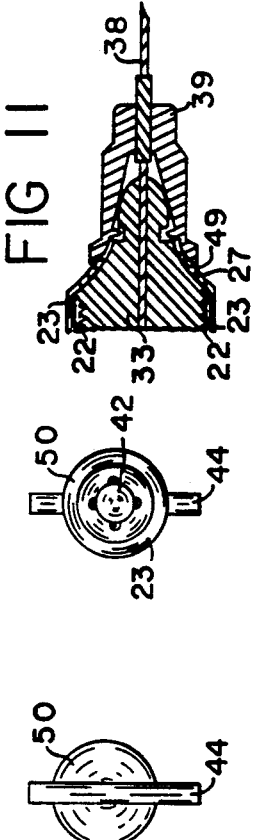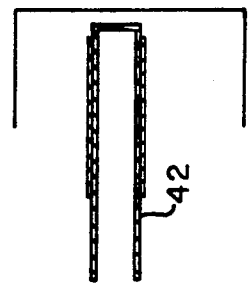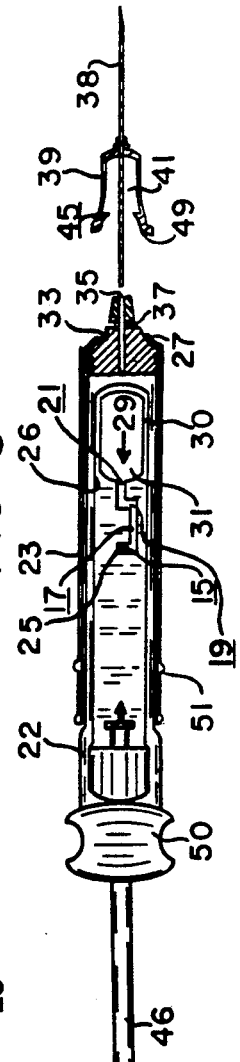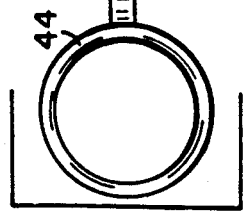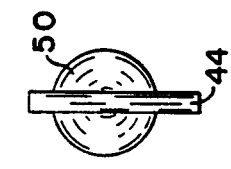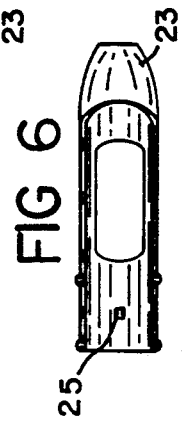

REMOTE CANNULA REMOVAL CARTRIDGE SYRINGE

FIELD OF THE INVENTION

This invention relates to cartridge syringes and more particularly to a design which improves the safety of the typical cartridge syringe, such as a dental syringe, by allowing the cannula to be removed by remote means.

BACKGROUND OF THE INVENTION

For many years the cartridge syringe has been used by dentists, physicians, veterinarians, and other related medical personnel. These syringes are characterized by a sterilisable tubular component into which a disposable unit dose medication vial can be inserted. A disposable needle mounted on a hub is screwed onto or into the front of the syringe so that the distal portion of the needle penetrates into the cartridge forming a fluid sealing engagement with the cartridge, and a partial opening by way of the cannula. The syringe is equipped with a plunger for expressing the contents of the cartridge through the cannula and into the patient.

Health professionals are becoming increasingly aware of the risks associated with use of the cartridge syringe. These risks include the possibility of physical injury by an inadvertent needle puncture and the more serious threat of cross-contamination and ensuing infection from an inadvertent "needle-stick" injury.

Contracting a serious or deadly disease such as ACQUIRED IMMUNE DEFICIENCY SYNDROME (A.I.D.S.) or Hepatitis B from a contaminated cartridge syringe needle is a very real possibility for healthcare workers. After penetration of an infected patient the cannula of the cartridge syringe is contaminated by the blood of the patient. When the syringe is removed from the patient it becomes an immediate source of infection which must be disposed of very carefully. It poses a serious threat to any individual who may come in contact with it.

Over the years healthcare workers have become more aware of the dangers associated with the cartridge syringe and a number of strategies have evolved to deal with the risks. Needle covers which fit over the cannulas have been used on dental cartridge syringes for many years to prevent needle-stick injuries. These covers or "caps" are removable parts of the needle hub and are inserted onto the front and rear aspects of the hub by the manufacturer prior to shipping. In use at the clinical site the dentist (or hygienist depending on state regulations) inserts an anesthetic cartridge into a dental syringe, removes the rear cap of a dental needle, screws the needle onto the front of a dental syringe, removes the front cap, and then proceeds with the dental injection. After the dental syringe is withdrawn from the mouth the operator may replace the front cap back onto the dental needle until the contaminated needle is either reused on the same patient, or disposed of.

The problem with this technique is that the practice of recapping the dental needle actually increases the risk of an inadvertent "needle-stick" injury since the operator's hands and fingers must come into close proximity with the contaminated cannula as they recap the needle.

"Recapping" the used dental needle is a usual practice in dentistry even though it has been discouraged by many public and private healthcare organizations. Recapping is still commonly practiced by dentists, physicians, and other health care personnel because in order to remove the needle from a reusable cartridge syringe it must be unscrewed from the very same threads to which it was initially screwed onto.

To avoid manual recapping but still permit the use of screw-on cartridge syringe needles some dental product manufacturers have developed dental needle receptacles. These receptacles give the operator of the dental syringe a margin of safety by increasing the operator's physical distance from the contaminated cannula during recapping or unscrewing procedures. They also typically provide a barrier around the receptacle so that hands and fingers will not slip and contact the needle when it is being removed from the syringe. One such recapping system is the "On Guard" system distributed by the Henry Schien Dental Supply Company of Port Washington, N.Y. The problem with this kind of recapping system is that it is unaesthetic, cumbersome, harder to use than it appears, and adds yet another element to the already overcrowded inventory of dental devices. In addition to the above mentioned drawbacks of recapping systems they have one other serious flaw; they are inconvenient to use.

Another method of improving the safety of the common cartridge syringe is to use a disposable unit dose syringe. In this case the needle, cartridge, and barrel are all disposed of together. This method of syringe use is costly, inconvenient, and creates a much larger volume of hazardous waste than traditional methods. It also allows the possibility of reuse by unauthorized persons since the elements of the syringe are all disposed of together in a bulk quantity.

Yet another method designed to improve the safety of the cartridge syringe involves using a needle cutting system which cuts off the cannula at the dental needle hub allowing it to fall into a protected container. This system is inconvenient in practice and may not be much safer since the cut surface of the needle that remains attached to the cartridge syringe is still sharp and possibly infectious. In use the needle hub with its cut end must still be removed from the syringe in the same manner as present art allows; by unscrewing it.

Turning now to patented prior art, a number of individuals have tried to deal with the risks of needle-stick injury and cross-contamination.

U.S. Pat. No. 3,648,695 to Bowen (1972) discloses a pressurized applicator for foamed medications which has an ejecting tip. This device cannot be used to aspirate fluids making it impossible to load medicines from dispensing vials, to draw blood or bodily fluids, or to aspirate as a precautionary action to determine the anatomical location of the cannula tip relative to venous and arterial structures.

The barrel of the pressurized applicator and its corresponding applicator tip are designed for foam applications and will not provide an adequate seal for fluids having low viscosities. Additionally, the high cost of manufacture severely limits the use of this device for routine delivery of medication.

U.S. Pat. No. 4,931,040 to Haber et al. (1990) shows a method by which the cannula bearing section of the syringe can be retracted within a cartridge. The major drawback of this design is that the cartridge and cannula must be manufactured as an integral part thereby complicating the process of manufacture and greatly increasing the cost of the device. This device permits only one use of the cannula prior to disposal even though multiple injections using more than one cartridge are typical. The cumbersome syringe must then be manipulated to retract the cannula.

U.S. Pat. No. 4,932,940 to Walker et al. (1990) shows a retractable needle guard for use with hypodermic syringes. Use of this device requires the operator to retract the guard by hand prior to giving an injection, to inject the patient while the guard is retracted by the surrounding tissues, or to manipulate the device in a manner that causes retraction of the guard just prior to injection. The disadvantage of this device with respect to the disclosed invention is that it does not apply to use of a cartridge type syringe. It also does not provide for convenient cannula disposal or separation of the infectious component from the syringe.

U.S. Pat. No. 4,950,253 to Jacobs shows a needle ejector structure which can be placed into a dental syringe after use to eject the needle hub from the front of the syringe. This device has some limited practicality but requires considerable manipulation of the syringe in order to eject the used needle hub. The act of removing the used anesthetic cartridge and placing the ejector into the barrel of the syringe adds risk to the operator since manipulation of the syringe near the cannula is necessary.

U.S. Pat. No. 4,986,811 to Thead et al. shows an apparatus for removing needles from syringes. This device is designed to unscrew a needle from a syringe. The major drawbacks to this device are that it is relatively expensive to produce and it adds a cumbersome machine component to the already crowded medical inventory. U.S. Pat. No. 4,986,812 to Perler (1991) shows a disposable syringe with a locking device to prevent reuse. It does not relate to convenient and safe disposal of the infectious cannula after use.

Unlike the above described prior art, the invention disclosed herein relates to safe, expeditious, convenient, and economical disposal of the cartridge syringe cannula without requiring the operator to risk injury by recapping or otherwise placing bodily parts near the contaminated cannula.

OBJECTS AND ADVANTAGES

It is therefore the object of the present invention to provide a safer method of cannula disposal following routine use of the typical cartridge syringe. Several objects and advantages of the present invention are:

(a) to provide a safe method of cannula removal without the necessity of placing fingers or other bodily parts on or near the contaminated cannula;

(b) to provide a means of cannula removal from the cartridge syringe whereby proper disposal of the contaminated cannula can occur immediately after syringe use;

(c) to provide separation of the cannula from the cartridge syringe so that it may be disposed of in a container of convenient size;

(d) to provide a convenient method of disposal that reduces the possibility of reassembly of the syringe components by unauthorized persons;

(e) to provide a method of cannula removal that is easily accomplished with minimal manipulation of the cartridge syringe;

(f) to provide a device which resembles in form and function the existing available cartridge syringes; and (g) to provide a device which is easy to manufacture based on existing materials and technology.

Further objects and advantages will become apparent based on consideration of the ensuing description and drawings.

BRIEF DESCRIPTION OF THE DRAWINGS

FIG. 1 is a side view in elevation of a conventional prior art syringe including a capped needle and a medication cartridge.

FIG. 2 is a perspective view of the present invention showing the syringe without a cartridge in place.

FIG. 3 is an end view of FIG. 2.

FIG. 4 is an end view of FIG. 2 taken from the opposite end of FIG. 3.

FIG. 5 is an exploded side view taken in elevation with a partial cut-away.

FIG. 6 is a side view of element 23 of FIG. 5.

FIG. 7 is a side view of element 23 of FIG. 5 rotated at 90 degrees.

FIG. 8 is a perspective view of element 23 of FIG. 5.

FIG. 9 is an end view of element 23 of FIG. 5.

FIG. 10 is an end view of element 23 of FIG. 5 taken from the opposite end.

FIG. 11 is an enlarged plan view of the hub and end of the first barrel.

DETAILED DESCRIPTION OF THE DRAWINGS

Referring now to FIGS. 1 through 11 wherein like characters refer to like elements throughout the various drawings, there is generally shown in FIG. 1 a conventional prior art syringe 20 such as a Cooke-Waite aspirating dental syringe. The syringe 20 is characterized by an elongated barrel 22 having a generally hollow interior as at 24 and an elongated slot 26 formed in the wall of the barrel through which a typical medication cartridge 28 may be inserted. Opposite the elongated slot 26 is another smaller slot which serves as a barrel window 30 for the purpose of the operator to see the cartridge 28 from the opposite side of the syringe during use. At the front wall of the barrel 22 is a needle receiver 32 which has a threaded outer surface 34 onto which a needle hub 36 may be reversibly affixed.

The needle hub 36 has affixed to it a cannula 38 with a sharp, pointed tip 40 and is surrounded by a needle cover 42 which is removable from the needle hub 36 prior to use.

At the distal aspect of the syringe 20 is found a thumbring 44 which is attached to a plunger rod 46. The plunger rod 46 is longitudinally slidable throughout the syringe. At the front end of the plunger rod 46 is a pointed barb 48. At the distal terminus of the barrel 22 is finger grasp 50 and a finger rest 52.

The cartridge 28 is fluid filled in its interior and sealed distally by a rubber stopper 54. The anterior wall of the cartridge 28 is sealed by a cartridge cap 56 that includes a membrane 58.

During syringe use the plunger rod 46 is retracted allowing for insertion of the cartridge 28 into the interior 24 of the barrel 22. The thumbring 44 is struck by hand to engage the barb 48 into the rubber stopper 54. The needle hub 36 is then screwed onto the needle receiver 32 such that the distal aspect of the cannula 38 passes through a hollow center of the needle receiver 32 and through the membrane 58 of the cartridge 28. Thus, a partial opening is formed between the interior of the cartridge 28 and the outside of the syringe 20 by way of the cannula 38. After use of the syringe the needle hub 36 is unscrewed from the needle receiver 32 and the plunger rod 46 is retracted to allow removal of the cartridge 28 from the syringe.

The present invention is shown in FIGS. 2 through 11. As shown in FIG. 5 a modified needle receiver 33, may be attached to a first syringe barrel 22 by the intermating of machine threads or by any other retentive means. The needle receiver 33 is characterized by a cylindrical form which tapers toward the front aspect of the syringe. The needle receiver 33 contains a longitudinal bore 35 to allow passage of the distal aspect of the cannula into the interior of the barrel 22. Circumscribed about the surface of the needle receiver 33 is a hub retention groove 37. A needle hub 39 is provided with a generally hollow distal concavity 41 and a cannula 38 affixed thereto. Preferably, the needle hub 39 is formed of material which is resilient or which has a "memory," such that, if displaced, the material tends to return to its original position. Circumscribed within the concavity 41 is a series of detents 45 for the purpose of providing engagement with the hub retention groove 37 when the needle hub 39 is placed onto the needle receiver 33.

FIG. 2 shows the needle hub 39 in place on the syringe and shows a series of expansion slots 47 which are provided on the body of the needle hub 39 to allow circumferential expansion of the needle hub 39 during its engagement and disengagement from the syringe. As shown in FIG. 5 an end flare 49 is provided on the needle hub 39 to slightly elevate the distal aspect of the hub from the needle receiver 33.

A second barrel 23 is shown in FIGS. 5 through 9. When attached to the syringe as in FIG. 5 it surrounds the first barrel 22 and is both rotatable and longitudinally slidable along the barrel 22. The second barrel 23 surrounds about one half of the circumference of the first barrel 22 leaving the elongated slot 26 exposed such that the medication cartridge may be inserted and removed from the syringe. The rear aspect of the second barrel 23 has a contour to provide a second barrel handle 51. The middle aspect of the second barrel 23 may have a window 31 corresponding to the first barrel window 30 for the convenience of the syringe operator. The front aspect of the second barrel 23 tapers to surround the middle aspect of the needle receiver 33. The front most aspect of the second barrel 23 forms an ejecting contour 27 which lies just distal to the end flare 49 of an attached needle hub.

FIG. 11 shows that the ejecting contour 27 substantially matches the inner contour of the end flare 49 such that protraction of the second barrel 23 causes expansion of the needle hub 39 with a concurrent forward ejection of the hub from the syringe.

As seen in FIG. 5 and other FIGURES, a retaining pin 25 is provided as a small raised cylindrical structure continuous with the inner aspect of the second barrel 23. A pin channel 29 comprises a segmented slotted space continuous with the inner cavity and barrel window 30 of the first barrel 22. It serves as an entry path for the pin 25 of the second barrel 23 and also as a retainer of the pin 25 for the purpose of imparting directional control of rotational and longitudinal movements of the second barrel 23 on the syringe.

The pin channel 29 is comprised of a series of segments, each of which imparts a certain reciprocal movement to the second barrel 23. A channel segment 21 allows the pin to enter the channel 29 at the barrel window 30, so that the second barrel 23 is partially retracted on the first barrel 22. A channel segment 19 allows for a rotation of the second barrel 23 on the first barrel 22 for alignment of the sheath pin 25 with a functional channel segment 17. The channel segment 17 imparts longitudinal motion of the second barrel 23 for the purpose of protraction and retraction of the second barrel 23 during use of the invention. A channel segment 15 provides a locking position for the second barrel 23 such that no longitudinal movement of the second barrel 23 will occur in this position.

OPERATION

To use the invention the second barrel 23 which is a component to the syringe itself is placed in the locked position with the sheath pin 25 lying within the channel segment 15. The needle hub 39 with its associated needle cover 42 may be snapped onto the needle receiver. The relationship of the attached needle hub 39 to the needle receiver 33 may best be observed in FIGS. 2 and 11. A cartridge may be inserted into the syringe either before or after the attachment of the hub. The cover 42 is then removed to allow injection.

As may be observed from FIG. 5, after normal use of the syringe the operator may rotate the second barrel 23 counterclockwise allowing the pin 25 to align with the functional channel segment 17. The operator may then protract the second barrel 23 causing the ejection contour 27 to engage the end flare 49 of the needle hub 39. The spreading of the needle hub 39 disengages the detents 45 from the hub retention groove 37 allowing the second barrel 23 to eject the needle hub 39 into a suitable container such as a SHARPS CONTAINER. The second barrel 23 may then be retracted and locked prior to sterilization and subsequent use.

Thus, immediately following injection or other use of the invention, the syringe may be held over a suitable disposal container for needles and the second barrel maybe rotated and protracted resulting in the ejection of the contaminated cannula. This accomplishes:

(a) an expeditious disposal of the cannula;

(b) a method of cannula disposal that does not require recapping or other dangerous manipulation of the syringe;

(c) a reduction in the volume of hazardous waste since the infectious portion of the syringe, the cannula, can be disposed of in a container of very small size;

(d) a convenient method of cannula disposal since the necessary hazardous waste containers can be made with less than a pint of volume and still dispose of a great quantity of infectious cannulas; and (e) a method of cannula disposal that causes separation of the cannula from the syringe allowing for disposal practices that discourage reassembly by unauthorized individuals.

SUMMARY AND SCOPE

Accordingly, the reader will see that the invention by its nature represents a significant improvement in the design and usage of the cartridge syringe. The risk of contracting a serious or lethal disease through an inadvertent needle-stick wound is lessened significantly when a clinician utilizes the invention and disposal methods as described above. Other risks to the public are averted as well since disposal methods are dramatically improved.

Although the above descriptions contain many specificities, these should not be construed as limiting the scope or spirit of the invention. Many variations of the shape and size of the invention are possible as are variations in the shape and size of the above described components. For example, the same invention might utilize a threaded needle receiver and an elastic or expandable needle hub such that the hub is screwed onto the syringe in a conventional manner, but ejected from the syringe by a second barrel or other ejection contour as described by the present invention.

Thus, the scope of the invention should be determined by the appended claims and their legal equivalents, rather than by the examples given.

What I claim and wish to protect by Letters Patent is:

1. A needle ejector structure comprising:
   a first elongated hollow barrel having a first and second end and being formed with a slot dimensioned to allow passage therethrough of a cartridge into and out of said barrel and having a needle hub receiver formed on said one end to removably secure a hub portion of a needle,
   a second elongated barrel having an open first and a second end having an outer wall dimensioned and disposed to surround and slidably engage the outer circumference of said first barrel and for communication with said needlehub and being movable to remove said needle hub from said hub receiver of said first barrel and having an elongated slot extending along said outer wall, dimensioned and disposed to allow passage therethrough of a cartridge,
   alignment means to align said slot of said first barrel with said slot of said second barrel,
   said first and second barrels each formed with additional elongated slots extending substantially opposite and parallel to said first elongated slots, said additional slots having different lengths than said first slots.

2. The device of claim 1 in which:
   said needle hub receiver has means to removably secure a hub portion of a needle comprising an annular groove circumscribed around the circumference of said receiver, and
   said needle hub is made of material having a memory formed with multiple detents separated by expansion slots.

3. The device of claim 2 in which said second end of said second barrel has an exterior tapered contour cooperating with an interior tapered contour of said detents of said hub, whereby, when said second end of said second barrel is urged into said hub, said detents of said hub expand out of and are forced from said annular groove of said hub receiver.

4. The device of claim 1 in which:
   said first barrel is formed with a channel, and
   said alignment means is a retaining pin mounted on the interior of said second barrel which is captured and guided by said channel in said first barrel.

5. The device of claim 4 in which said channel is substantially U-shaped with its common leg being substantially lengthwise of said barrel and its two uncommon legs being substantially crosswise, whereby, when said pin is in the uncommon leg of said channel furthest from said second end of said first barrel, said second barrel is in a locked position in relation to its sliding relationship to said first barrel and when said pin is in said lengthwise common leg of said channel, said second barrel is slidable lengthwise on said first barrel.

6. The device of claim 5 in which said channel is in communication with said slot in said first barrel.

7. The device of claim 1 in which said second barrel is partially supported by the concentricity of said first and second barrels at their frontmost ends.

8. A syringe comprising:
   a cylindrical barrel having an axis,
   a needle having a hub releasably mountable on one end of said barrel,
   means encircling said barrel and selectably movable to disconnect said needle hub from said one end of said barrel,
   lock means releasably locking said means encircling said barrel to prevent inadvertent release of said hub,
   said lock means being a slot extending parallel to the axis of said barrel and having a lateral portion extending perpendicular to said axis, and
   means slideable along said slot carried by said means encircling said barrel.

9. The syringe of claim 8 wherein:
   said needle hub is formed with a conical recess engageable with said one end of said barrel, and
   said last named means is formed with a conical end portion insertable into said recess to disengage said needle hub from said barrel.

10. The syringe of claim 8 wherein said needle hub is formed of resilient material.

11. The syringe of claim 8 wherein said needle hub is formed of material having a memory.

12. A syringe comprising:
    a cylindrical barrel,
    a needle having a hub releasably mountable on one end of said barrel,
    means encircling said barrel and selectably movable to disconnect said needle hub from said one end of said barrel,
    said needle hub being formed with a flared end releasably engaging said one end of said barrel, and
    said means encircling said barrel is insertable into said flared end and serves to expand said flared end to disengage said needle hub from said one end of said barrel.

13. A needle ejector structure comprising:
    a first elongated hollow barrel having a first and second end and being formed with a slot dimensioned to allow passage therethrough of a cartridge into and out of said barrel and having a needle hub receiver formed on said one end to removably secure a hub portion of a needle,
    a second elongated barrel having an open first and a second end having an outer wall dimensioned and disposed to surround and slidably engage the outer circumference. of said first barrel and for communication with said needlehub and being movable to remove said needle hub from said hub receiver of said first barrel and having an elongated slot extending along said outer wall dimensioned and disposed to allow passage therethrough of a cartridge,
    alignment means to align said slot of said first barrel with said slot. of said second barrel,
    said first barrel being formed with a channel, said alignment means is a retaining pin mounted on the interior of said second barrel which is captured and guided by said channel in said first barrel,
    said channel being substantially U-shaped with its common leg being substantially lengthwise of said barrel and its two uncommon legs being substantially crosswise, whereby, when said pin is in the uncommon leg of said channel farthest from said second end of said first barrel, said second barrel is in a locked position in relation to its sliding relationship to said first barrel and when said pin is in said lengthwise common leg of said channel, said second barrel is slideable lengthwise on said first barrel.

14. The device of claim 13 in which said channel is in communication with said slot in said first barrel.

15. A syringe comprising:
a cylindrical barrel,
a needle having a hub releasably mountable on one end of said barrel,
means encircling said barrel and selectably movable to disconnect said needle hub from said one end of said barrel,
said needle hub being formed with a conical recess engageable with said one end of said barrel, and
said last means encircling said barrel is formed with a conical end portion insertable into said recess to disengage said needle hub from said barrel.

* * * * *